(12) United States Patent
Apelqvist et al.

(10) Patent No.: US 7,347,105 B2
(45) Date of Patent: Mar. 25, 2008

(54) METHOD FOR THE ANALYSIS OF A TEST SPECIMEN OF REDUCIBLE MATERIAL THAT CONTAINS IRON

(75) Inventors: Anders Apelqvist, Malmberget (SE); Kjell-Ove Mickelsson, Koskullskulle (SE); Seija Forsmo, Malmberget (SE); Urban Holmdahl, Piteå (SE)

(73) Assignee: Luossavaara-Kiirunavaara AB, Lulea (SE)

( * ) Notice: Subject to any disclaimer, the term of this patent is extended or adjusted under 35 U.S.C. 154(b) by 12 days.

(21) Appl. No.: 11/322,647

(22) Filed: Jan. 3, 2006

(65) Prior Publication Data

US 2006/0159614 A1    Jul. 20, 2006

(30) Foreign Application Priority Data

Jan. 4, 2005  (SE) .................................. 0500018

(51) Int. Cl.
*G01N 3/08* (2006.01)
(52) U.S. Cl. .............................. 73/818; 73/821; 73/825
(58) Field of Classification Search ................. 73/818, 73/821, 825
See application file for complete search history.

(56) References Cited

U.S. PATENT DOCUMENTS 3,580,060 A * 5/1971 Huskey ........................ 73/816
5,459,767 A * 10/1995 Lessing ....................... 376/245
5,633,468 A * 5/1997 Powers et al. ................ 73/801

* cited by examiner

*Primary Examiner*—Edward Lefkowitz
*Assistant Examiner*—Freddie Kirkland, III
(74) *Attorney, Agent, or Firm*—Nixon & Vanderhye P.C.

(57) ABSTRACT

A method for the analysis of the properties of a test specimen comprises: arranging a test specimen between contact surfaces; continuously reducing the distance between the contact surfaces; measuring the diameter of the test specimen when the test specimen makes contact with the contact surfaces; further displacing the contact surfaces in a direction towards each other during the compression of the test specimen until the test specimen disintegrates; storing and continuously recording the force that is applied to the test specimen and the time; recording the maximum forces at all the points of disintegration of the test specimen; increasing the distance between the contact surfaces; and removing the test specimen.

13 Claims, 3 Drawing Sheets

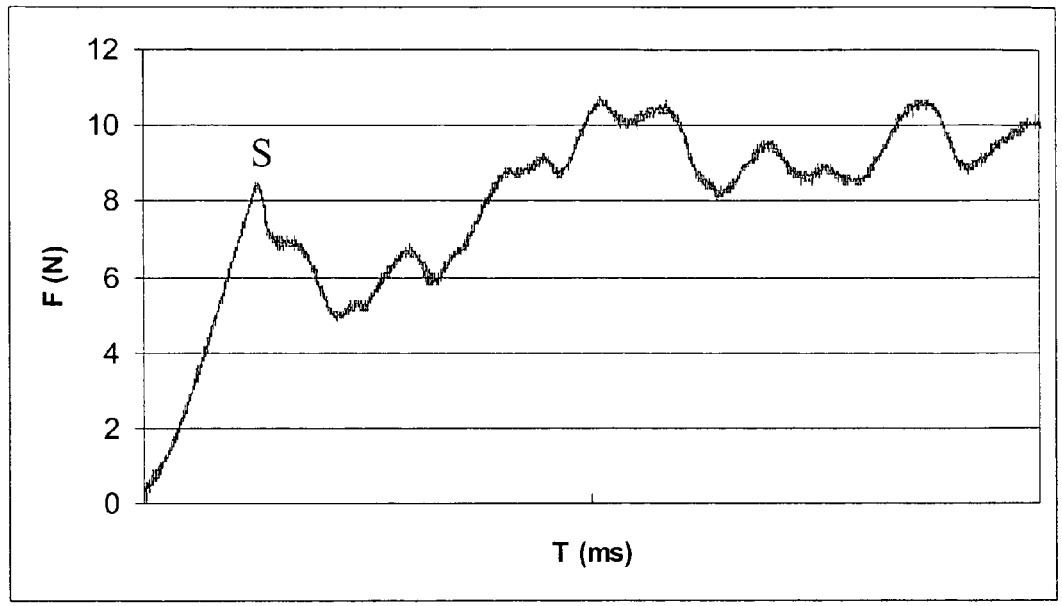
Figure 3. Force as a function of time during the testing of a raw pellet.
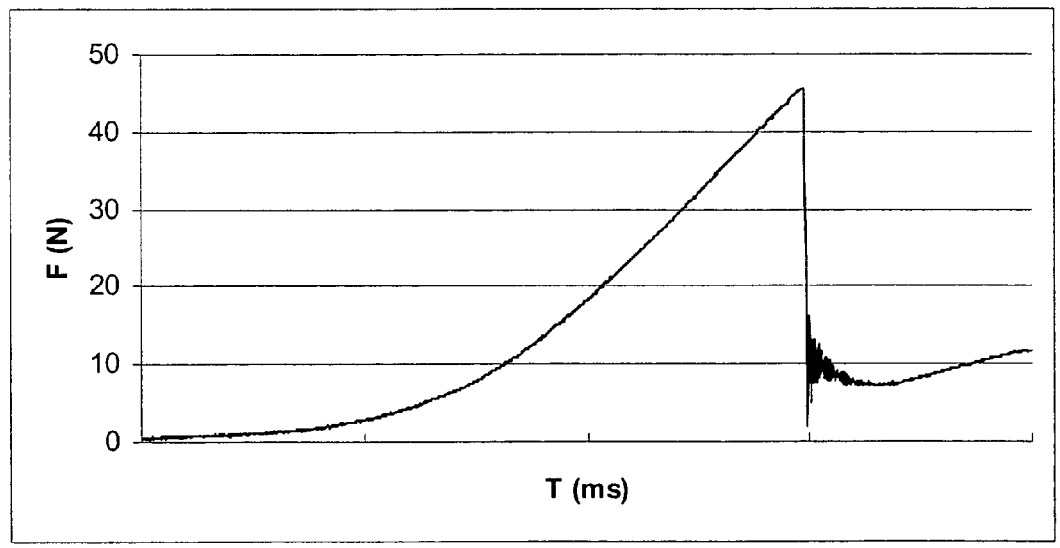
Figure 4. Force as a function of time for a raw pellet showing Class A disintegration.

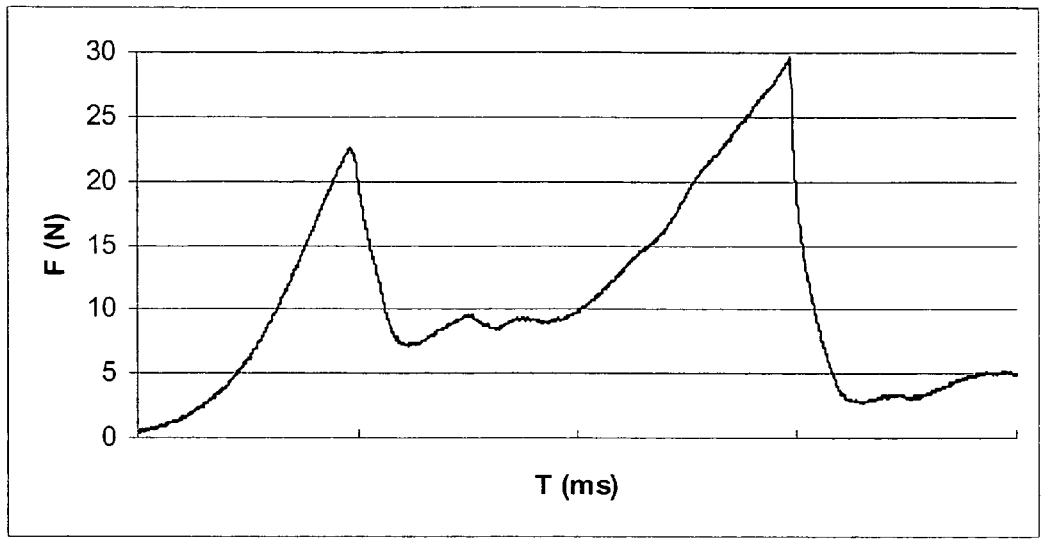
Figure 5. Force as a function of time for a raw pellet showing Class B disintegration.
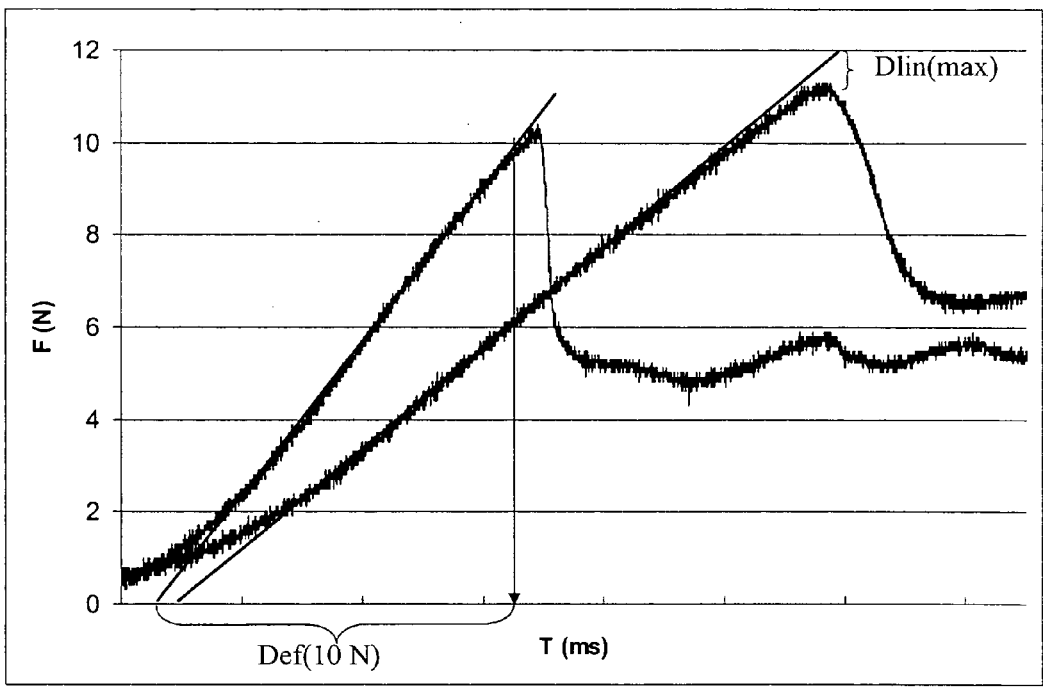
Figure 6. Force as a function of time for two moist raw pellets showing Class C disintegration. The figure shows also an example of the calculation of the magnitude of deformation at a force of 10 N (Def(10N)) and the calculation of deviation from linearity (Dlin(max)).

METHOD FOR THE ANALYSIS OF A TEST SPECIMEN OF REDUCIBLE MATERIAL THAT CONTAINS IRON

This application is a new U.S. patent application claiming benefit of SE 0500018-7, filed 4 Jan. 2005, the entire content of which is hereby incorporated by reference.

BACKGROUND AND SUMMARY OF THE INVENTION

The present invention concerns a method for the analysis of the properties of a reducible test specimen that contains iron of the type raw pellet or pellet during the manufacture of raw pellets or pellets, for the optimisation of the pelletization process and a subsequent extraction of iron.

Extraction of metallic iron normally takes place through the reduction of iron oxide in a blast furnace or through its direct reduction in a direct reduction furnace. The iron oxide in the form of pellets comes into contact with a reducing gas, whereby the iron oxide is reduced to metallic iron in the form of molten iron, or what is known as sponge iron. The temperature of the reducing gas in the direct reduction process is approximately 800-950° C. If the pellets disintegrate during the reduction process, the contact of the reducing gas with the iron oxide is made more difficult, resulting in uneven operation and reduced productivity. For this reason, it is desired to obtain pellets of an even and high strength. The term "pellets" is here used to denote bodies composed of a reducible material containing iron that are in the form of agglomerates of finely divided material. Chemically pure iron ore concentrate that has been milled to a suitable size is mixed during the manufacture of pellets with an additive, and the mixture is then filtered to give a moist fibre cake. The moisture content of the fibre cake normally lies in the interval from 8 to 9% by weight. The moist filtered material is mixed with a binding agent and is rolled by known methods, for example, using rolling drums or rolling disks to give raw balls, known as green pellets, having a diameter of approximately 10-15 mm. The raw pellets are further processed by drying at an elevated temperature, in order subsequently to be sintered at high temperature to hardened pellets.

Moist raw pellets are weak and normally demonstrate a compressive strength of approximately 10 N/pellet. The low strength means that the pellets break easily. Broken pellets are separated out by sieving before the raw pellets are fed into the pelletizing machine, but raw pellets may break also after the sieving. The means that the penetrating ability of the gas in the bed of raw pellets during the process of forming pellets is reduced, and this in turn means that the drying, and the oxidation (if the iron ore concentrate is magnetite), cannot take place in an efficient and homogeneous manner. Furthermore, raw pellets are plastic, i.e. they can be deformed by pressure, and this further reduces the penetrability of the bed, since deformed pellets will close the spaces that form between pellets that have a high strength, and through which spaces the gas is to pass.

When moist raw pellets are dried, binding agent and any other dissolved or finely divided material present collects at the points of contact between the particles that are components of the raw pellets. This creates new bonds, whereby a dry raw pellet demonstrates an increased strength when binding agent is used, typically in the interval 20-60 N/pellet.

If the iron ore concentrate is magnetite, the raw pellets are oxidised to hematite during the pelletization process. Further points of contact are formed between the particles that are components of the raw pellets, whereby the compressive strength typically amounts to approximately 500-800 N/pellet, although also other values may arise.

After the sintering, which normally takes place at approximately 1,300° C., the sintered pellet obtains a compressive strength greater than 2,000 N/pellet. It is important for several reasons to obtain a high and even strength of the pellets. In addition to the effects during the reduction process described above, also the strength during handling during transport is important. The final strength of the pellets is determined to a major extent by the strength of the raw pellets at the beginning of the pelletization process.

Different moisture contents, the fineness of the starting material, the amount of binding agent and the conditions during the mixing process are examples of parameters that give different strengths. A higher strength of the raw pellets and the pellets means that the pelletization process can be carried out at a higher capacity. Lower amounts of fines are created during the transport, and the productivity of the reduction process will be higher. The requirements for an even and high quality of the pellets is increasing, and this means that feedback between the quality of the pellets and the properties of the raw pellets is becoming ever more important. Random samples from the pellet production are taken in order to determine the strength of the final pellets used in the extraction of iron. The random samples are subjected to different types of test. Test methods for non-sintered pellets and for moist and dry raw pellets, however, have not been reliable, and there is for this reason a need for an efficient and reliable test method.

Arrangements for testing the hardness of test specimens are previously known. A common method of testing moist raw pellets is to drop the raw pellet a number of times from a pre-determined height. The number of times that the raw pellets can be dropped from that height without breaking gives the result of the test. The disadvantage of this method is that the result depends of the person conducting the test, i.e. the result can be unconsciously influenced by the person who carries out the test.

An arrangement for testing moist and dried raw pellets and pellets has been designed in such a manner that it can press the raw pellet or pellet to breakage through the application of a piston with increasing force until the raw pellet or pellet breaks. Reading takes place at the moment of breakage, either manually on a meter or automatically, as a maximum value before the diameter has been reduced by a certain percentage. The value of the force read is entered into a table. The disadvantage of this is that the applied force is not recorded during the complete pressure application process, and for this reason only information about the maximum force that was applied during the complete pressure application process can be obtained. It has proven to be the case that the maximum force can arise once the formation of cracks has begun in the raw pellet or pellets and thus in this manner give an erroneous image of the strength. Visual reading is imprecise and depends on the person who performs it. A further disadvantage of this arrangement is that it is designed in such a manner that the weak moist and dried raw pellets must be manually inserted one at a time.

If the moist, filtered material can be given an optimal moisture content, it demonstrates a sufficiently rapid growth during the rolling procedure, i.e. during the formation of raw pellets, maximal strength of the raw pellets formed, and sufficiently high plasticity such that it can survive the handling, and this is of major significance for the subsequent pelletization process.

One aim of the present invention is thus to provide an arrangement and a method for the analysis of properties of test specimens of reducible material that contains iron in its sintered or non-sintered form in the form of raw pellets and pellets, and to provide a subsequent report.

These aims are achieved through a method that demonstrates the properties and characteristics that are defined in the subsequent claims.

BRIEF DESCRIPTION OF THE DRAWINGS

Example embodiments selected will be described below, with reference to the attached drawings, of which FIGS. 3-6 show examples of graphical curves that have been plotted of the collected measured values.

DETAILED DESCRIPTION OF PREFERRED EMBODIMENTS

Figure 1:
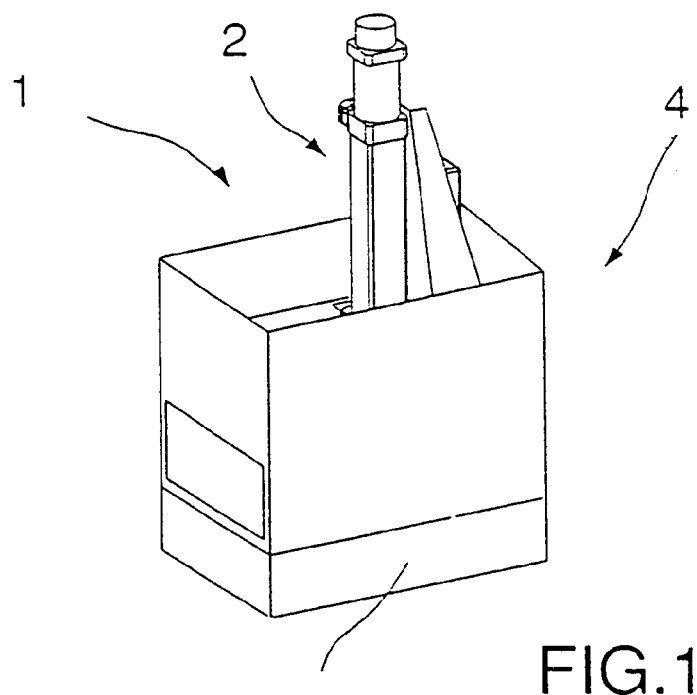
FIG. 1 shows a press for compression according to the invention.

The arrangement shown in FIG. 1 comprises a press 1 for test specimens A of reducible material that contains iron, in the form of green pellets, i.e. moist or dried raw pellets, or sintered pellets. The press 1 comprises a frame 2 with a base 3 in the form of a bottom part. A cover 4 is arranged over the frame 2 in the form of a pair of essentially vertical walls 5 at a distance from each other and a back piece 6. The cover 4 is provided with openings 7 for the connection of the press 1 with control and recording apparatus in the form of, for example, a computer, PLC or similar (not shown in the drawings).

Figure 2:
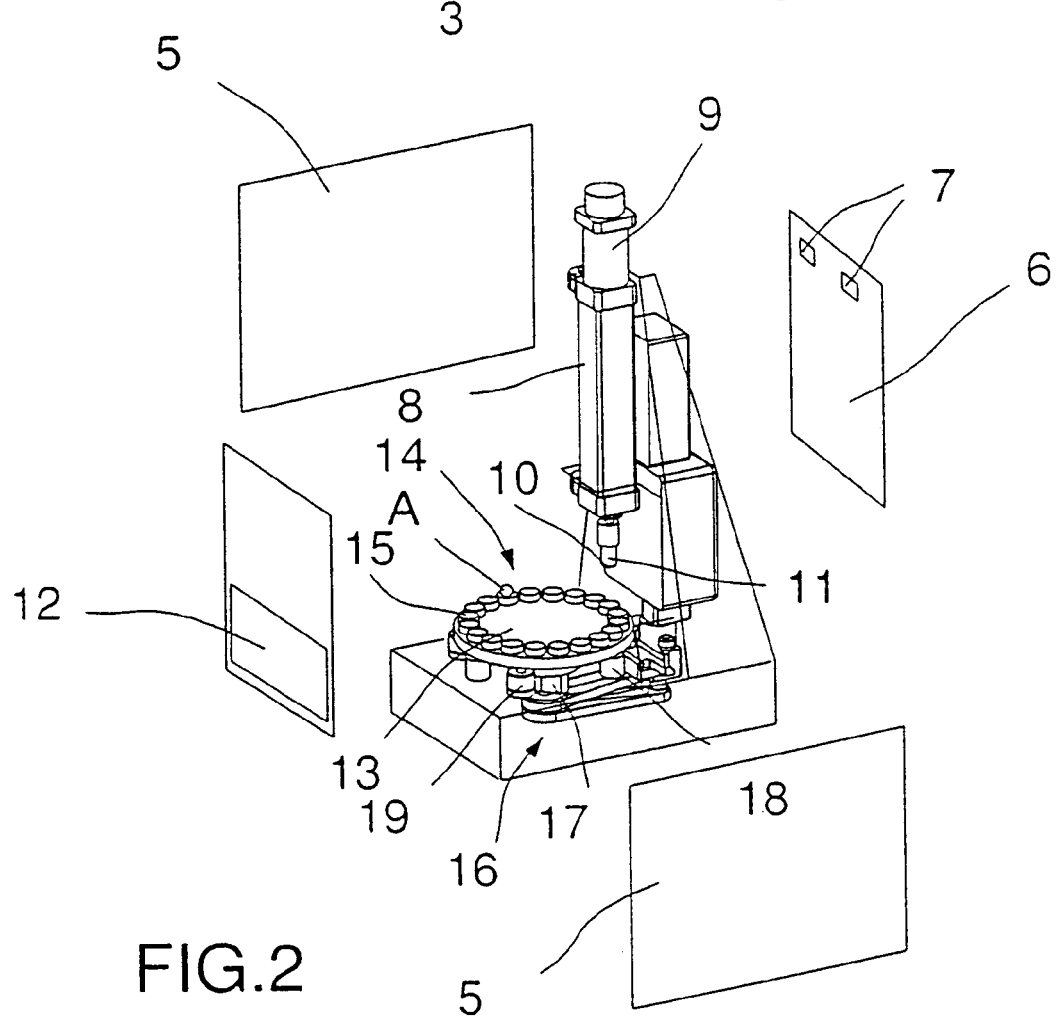
FIG. 2 shows the press from FIG. 1 with its cover removed.

A first device is arranged between the vertical walls 5, as is shown in FIG. 2, with a contact surface in the form of a pressure device 8 that can be displaced under control between a first withdrawn end position and a second extended position. The pressure device comprises, for example, a piston or a punch with a force that has been adapted for the current field of application. A force in the interval 0-100 N is used when testing raw pellets, while the measurement area is selected when testing sintered pellets such that the maximal force lies between 100-3,300 N. The speed of the pressure device 8 is set at between 2-50 mm/min in the preferred embodiment, and the distance of displacement of the pressure device 8 is set to 100 mm. The said speed and distance are regulated via an electric, hydraulic or pneumatic motor 9 and they are controlled by the said computer through a sensor.

A contact sensor 11 is arranged at the free end of the pressure device 8, at its surface 10 of contact, and it is intended that the contact sensor record the contact of the pressure device 8 with the surface of the pellet A. The pressure device may be driven with two or more different speeds in sequence, in order to minimise the time taken for pressure to be applied. The pressure device is fed forwards rapidly from its upper end position in a direction towards the test specimen. Rapid feed is ended before the contact sensor makes contact with the test specimen, at a distance from the end position that has been pre-determined. The contact sensor is used to measure the diameter of the test specimen, which diameter is read when the contact sensor makes contact with the test specimen. The cover 4 is furthermore provided with an opening 12 for access to a second device, arranged on the base 3, with a contact surface 13 in the form of an element having the shape of a platform, a disk, for example. This element can be rotated, preferably in the horizontal plane.

The disk 13 demonstrates on its surface 14 that faces the pressure device 8 a number of depressions or cavities 15, in which it is intended that test specimens A are placed in a manner that keeps them in place. The depressions 15 are symmetrically located at mutual distances from each other around the outer edge of the disk 13. The number of depressions 15 is 20 in this embodiment, but it must be realised that the number of depressions may be larger or smaller. The depressions 15 have a size that can accommodate a test specimen having a diameter in the interval 1-30 mm, a suggested interval is 5-15 mm. It is an advantage if the depressions have the form of bowls, whereby the test specimens can be displaced towards the centre of the depression in a simple manner during deployment. The disk in another embodiment has been designed with continuous walls or collars that surround the depressions. The task of the collars is to prevent dust and fragments from being spread inside the equipment when the test specimens are broken. The depressions in a further embodiment are only partially surrounded by collars in order to make possible an optical study of the breakage of the test specimens during the pressurisation procedure.

The disk 13 is arranged with a turning mechanism 16, such as a motor, a disc driven by a drive belt or a toothed wheel that is driven by a motor, and it may be disassembled to allow the depressions 15 of the disk 13 to be cleaned and to allow new test specimens to be placed into the depressions. The turning mechanism 16 is provided with an angle sensor in order to locate the depression of the disc at the correct location relative to the direction of motion of the pressure device 8.

Furthermore, a rotation coupling 17 is arranged between the turning mechanism 16 and the disk 13. The rotation coupling 17 is constructed with a loose structure or with play. The function of the looseness or play is to free the disk 13 from the turning mechanism 16 when the depression 15 of the disk is positioned in the correct manner, and in this way to free the mechanical contact between the disk 13 and the turning mechanism 16. This is necessary in order to avoid errors in the collection of data. The rotation of the disk 13 is coupled to the motion of the pressure device 8 in such a manner that when the pressure device 8 moves away from the disk 13, this disk is moved forward one step in order to position a new test specimen A in line with the direction of motion of the pressure device 8.

The contact surface 13 of the second device comprises in another embodiment an extended element with the form of a platform intended to receive a number of test specimens and to be moved forward, in its longitudinal direction, one step during the pressing operation.

It should be realised that both of the contact surfaces may in another embodiment be displaceable in a direction towards and away from each other, or that only the contact surface having the form of a platform may be displaceable in a direction towards the first contact surface.

At least one loading cell 18 is arranged in line with the pressure device 8 and the disk 13 that can be displaced in a direction along the direction of motion of the pressure device 8. The loading cell is selected in the same manner as the pressure device with respect to its field of operation. A loading cell with a measurement range in the interval, for example, 0-100 N is used when testing moist or dried raw pellets, while the measurement range is selected to lie between, for example, 0-1,000 N when testing partially hardened pellets. It should be realised that the measurement range of the loading cell is selected in order to correspond to the putative loading forces that can arise. The loading cell 18 is synchronised with the motions of the pressure device 8 and the disk 13, whereby the value of the load that is applied to the test specimen A is transferred to the computer.

The disk 13 is supported at three points distributed over the surface 14 of the disk that faces away from the pressure device 8, distributed as, for example, a triangle, in which one point comprises the loading cell 18 and the two other points comprise mechanical supports 19. The loading cell 18 is located in a line with the direction of motion of the pressure device 8 at the position at which the depressions 15 of the disk 13 are placed before each test. Loading cells 18 are arranged in another embodiment at two or at all of the support points. Sources of error during the collection of data are avoided if a loading cell is arranged at each support point, which error may arise if the test specimen is located obliquely in the depression, i.e. if the test specimen is not located centrally in the depression.

The loading cell 18 is in another embodiment arranged at the pressure device 8. The pressing procedure can in such an embodiment be the same as that described above, but it should be realised that the pressure device 8 may be arranged also as a fixed device whereby the surface of contact 13 is first moved forward one step in order to position a test specimen A at the correct position, after which the surface of contact 13 is displaced in a direction towards the pressure device 8 for the compression of the test specimen A.

The loading cell 18, the disk 13 and the pressure device 8 are, as has been described above, connected to a computer, to a PLC, or to similar equipment. A test specimen is placed during testing in each depression after which the testing is sequentially carried out on all test specimens. The computer collects the measured values through the loading cell and the contact sensors of the pressure device, and stores these values in a storage medium in the form of a memory, for example a hard disk of the computer, in a manner that is previously known, after which a measurement file is generated. The measured values that are collected are, for example, sequence number of the test specimen A that is being tested, continuous measurement of the force that is applied by the pressure device 8 from the moment at which the pressure device makes contact with the test specimen until the test specimen disintegrates, i.e. until the pressure device has reached a specified reversal position, the magnitude of the distance between the pressure device 8 and the disk 13 when the pressure device makes contact with the test specimen, and the voltage across the contact sensor 11. It should be realised that also other values may be collected, depending of the aim and nature of the analysis. The rate at which the values are collected in this embodiment is 1,000 per second, but it may be 200,000 per second The measured values that are collected are collated to a numerical report and to a graphical report. The numerical report and the underlying information for this report are automatically created after the compression of all test specimens on a disk. Examples of the values that are presented in tabular form are diameter, force, classification as defined by the manner in which it disintegrates, deformation and any deviation from linearity.

The graphical report illustrates the force process during the pressure procedure and the crushing of each test specimen with respect to the motion of the pressure device.

Examples of the use of the measured values will now be shown. The term "test specimen" has in certain cases been replaced by the term "raw pellet" or "pellet" for reasons of clarity.

During analysis of the compressive strength of the raw pellet or pellet with the aid of the measured values that have been collected, the graphical curve of force and time that has been plotted is studied, see FIG. 3. The graph is plotted with force in Newtons (N) along the Y-axis, and time in milliseconds (ms) along the X-axis, in the same manner for testing not only moist or dry raw pellets but also sintered or non-sintered pellets. The pressure increases with increasing force, until the pellet breaks for the first time. The pressure can subsequently start to rise again and several subsequent breaking events can take place. When the pellet breaks and the pressure applied falls, the curve turns downwards in a direction towards the X-axis. The breakage point, or disintegration point, S, is the maximum pressure before a predefined fall in pressure occurs for the first time, this fall in pressure may be, for example, 10% of the maximum pressure. The magnitude of the crack in the test specimens that is defined as "breakage" can in this way be defined.

The magnitude of the fall in pressure relative to the maximum pressure at the point of disintegration is used to classify the test specimens into different classes. The classification reflects the pattern of the disintegration process of the test specimens. If the test specimen disintegrates into a small number of large pieces the fall in pressure will be large, as great as 80% or greater, for example, and the pellets are classified as "Class A", see FIG. 4. If the disintegration takes place in stages, this may depend on the raw pellet being built up in such a manner that a number of shells have been applied onto each other. When such a raw pellet is tested, the bonds between the shells may be weaker and the raw pellet disintegrates in several stages. The fall in pressure for a stepwise disintegration will be smaller, between, for example, 50% and 80% of the maximum pressure, and the pellets are classified as belonging to "Class B", see FIG. 5. The disintegration may also take place slowly such that the pressure curve displays a large curvature at the point of disintegration. This behaviour is typical of moist raw pellets, which have a high fluid saturation. The fall in pressure can typically be between 10% and 50% of the maximum pressure, and the pellets are classified as belonging to "Class C". Class C disintegration is typical also for powdery disintegration in which the moisture content of the raw pellets is too low, but in this case the fall in pressure on the pressure curve will be more distinct. One example of each type of disintegration is shown in FIG. 6. Also other values of the fall in pressure may be used to classify the test specimens.

A moist raw pellet is deformed through a slow compression with a residual deformation as a result. Due to the fact that the particles start to slide relative to each other, while retaining their mutual bonds, the cross-section of the pellet changes from circular to elliptical. As has been described earlier, this property is a disadvantage for the subsequent pelletization process since deformed raw pellets close the spaces between the raw pellets, through which spaces the gas is to pass, leading to an increase in the fall of pressure and an increase in the difficulty of oxidation. Since raw pellets demonstrate different strengths and different forms of graph when the pressure approaches that at the point of disintegration, the deformation cannot be directly read from the pressure graph. The pressure increases linearly right up to the point of disintegration in certain cases. Breakage of bonds may occur in other cases before the point of disintegration is reached, and this leads to a curvature of the graph.

When analysing the deformation of the test specimen with the aid of the measured values that have been collected, a regression line is drawn in the form of a tangent to the curve between two determined values, in this case between 3 and 8 N, as shown in FIG. 6. The limiting values are selected such that the pressure curve between these two values shows linear growth. Deformation of raw pellets following slow application of pressure up to 10 N can be read by reading off the value on the X-axis at that point at which 10 N on the Y-axis cuts the regression line. The distance along the X-axis from this point to the point at which the regression line cuts the X-axis is converted to micrometers whereby the deformation of the test specimen can be determined. If the compressive strength of the raw pellet is lower than 10 N, the regression line is extended beyond 10 N in order to read the deformation.

The magnitude of the deformation is influenced by, among other factors, the levels of moisture and of porosity of the raw pellets and the fineness of structure of the raw material and the form of its particles. According to FIG. 6, in which pressure force (N) has been plotted along the Y-axis and time (ms) along the X-axis, the deviation of the pressure curve from linearity (Dlin(max)) is measured at the maximum pressure at the point of disintegration, and this describes the form of the curve. The deviation from linearity will be equal to zero in the case in which the curve is fully linear. The deviation from linearity is a positive value if the pressure curve bends before the point of disintegration. If the calculated deviation from linearity has a negative value, this is a signal that the tangent has been erroneously drawn and thus that the calculated deformation value is erroneous. The deviation from linearity can thus be used to check that the tangent has been correctly drawn and that the calculation of deformation has been correctly carried out. If the deviation from linearity is negative, for example, less than −1 N, the tangent can be redrawn by moving the upper point higher or lower along the pressure scale, depending on what the strength of the raw pellets permits. The values of deformation that are associated with a negative deviation from linearity, for example less than −1 N, can be omitted from calculations of the mean value.

The present invention is not limited to what has been described above and shown in the drawings: it can be changed and modified in a number of different ways within the scope of the innovative concept specified herein.

The invention claimed is:

1. A method for the analysis of properties of a test specimen of reducible material that contains iron of the type raw pellet or pellet during the production of raw pellets or pellets for the optimization of the pelletization process and the subsequent extraction of iron by the use of an arrangement that demonstrates a first device and a second device spaced a distance from each other that can be displaced relative to each other by a force applied to at least one of the devices, said first and second devices including contact surfaces facing each other, which method comprises:
   a) arranging a test specimen between the contact surfaces;
   b) continuously reducing the distance between the contact surfaces;
   c) measuring the diameter of the test specimen when the test specimen makes contact with the contact surfaces;
   d) further displacing the contact surfaces in a direction towards each other during compression of the test specimen until the test specimen disintegrates;
   e) continuously recording and storing (i) the force that is applied to the test specimen and (ii) time;
   f) recording the maximum forces at all points of disintegration of the test specimen;
   g) presenting the measured values collected in real time;
   h) increasing the distance between the contact surfaces; and
   i) removing the test specimen or remnants thereof.

2. The method according to claim 1, whereby the test specimen is classified according to a fall in pressure that arises after the said point of disintegration.

3. The method according to claim 1, whereby the measured values collected are presented numerically in the form of tables.

4. The method according to claim 1, whereby the measured values collected are presented graphically in the form of diagrams.

5. The method according to claim 1, whereby several test specimens are compressed in sequence, while measurement data is collected.

6. The method according to claim 1, wherein the measured values are used for the production of a graph, a regression line is drawn on the graph between two points on the Y-axis whose values have been pre-determined, and the value on the X-axis at the point at which a pre-determined value on the Y-axis intersects the regression line is drawn from the value at the point at which the regression line intersects with the X-axis, whereby the difference is used as a measure of the deformation of the test specimen during slow compression of the test specimen to a force, the value of which has been pre-determined.

7. The method according to claim 6, whereby the deviation from linearity of the pressure curve is read by the difference along the Y-direction between the point of disintegration and the regression line.

8. A method for the analysis of properties of a test specimen of reducible material that contains iron of the type raw pellet or pellet during the production of raw pellets or pellets for the optimization of the pelletization process and the subsequent extraction of iron by the use of an arrangement that demonstrates a first device and a second device spaced a distance from each other that can be displaced relative to each other by a force applied to at least one of the devices, said first and second devices including contact surfaces facing each other, which method comprises:
   a) arranging a test specimen between the contact surfaces;
   b) continuously reducing the distance between the contact surfaces;
   c) measuring the diameter of the test specimen when the test specimen makes contact with the contact surfaces;
   d) further displacing the contact surfaces in a direction towards each other during compression of the test specimen until the test specimen disintegrates;
   e) continuously recording and storing (i) the force that is applied to the test specimen and (ii) time;
   f) recording the maximum forces at all points of disintegration of the test specimen;
   g) increasing the distance between the contact surfaces; and
   h) removing the test specimen or remnants thereof,
   wherein the method further comprises compressing several test specimens in sequence, while measurement data is collected.

9. The method according to claim 8, whereby the test specimen is classified according to a fall in pressure that arises after the said point of disintegration.

10. The method according to claim 8, whereby the measured values collected are presented numerically in the form of tables.

11. The method according to claim 8, whereby the measured values collected are presented graphically in the form of diagrams.

12. A method for the analysis of properties of a test specimen of reducible material that contains iron of the type raw pellet or pellet during the production of raw pellets or pellets for the optimization of the pelletization process and the subsequent extraction of iron by the use of an arrangement that demonstrates a first device and a second device spaced a distance from each other that can be displaced relative to each other by a force applied to at least one of the devices, said first and second devices including contact surfaces facing each other, which method comprises:

a) arranging a test specimen between the contact surfaces;
 b) continuously reducing the distance between the contact surfaces;
 c) measuring the diameter of the test specimen when the test specimen makes contact with the contact surfaces;
 d) further displacing the contact surfaces in a direction towards each other during compression of the test specimen until the test specimen disintegrates;
 e) continuously recording and storing (i) the force that is applied to the test specimen and (ii) time;
 f) recording the maximum forces at all points of disintegration of the test specimen;
 g) increasing the distance between the contact surfaces; and
 h) removing the test specimen or remnants thereof, wherein the measured values are used for the production of a graph, a regression line is drawn on the graph between two points on the Y-axis whose values have been pre-determined, and the value on the X-axis at the point at which a pre-determined value on the Y-axis intersects the regression line is drawn from the value at the point at which the regression line intersects with the X-axis, whereby the difference is used as a measure of the deformation of the test specimen during slow compression of the test specimen to a force, the value of which has been pre-determined.

13. The method according to claim 12, whereby the deviation from linearity of the pressure curve is read by the difference along the Y-direction between the point of disintegration and the regression line.

* * * * *